US00PP35202P2

(12) United States Plant Patent
Fazio et al.

(10) Patent No.: US PP35,202 P2
(45) Date of Patent: Jun. 6, 2023

(54) APPLE TREE ROOTSTOCK NAMED 'G.66'

(50) Latin Name: ***Malus domestica* X *Malus robusta* hybrid**
Varietal Denomination: G.66

(71) Applicants: Cornell University, Ithaca, NY (US); The United States of America, as Represented by the Secretary of Agriculture, Washington, DC (US)

(72) Inventors: Gennaro Fazio, Geneva, NY (US); Terence Lee Robinson, Geneva, NY (US); Herbert Sanders Aldwinckle, Geneva, NY (US); James N. Cummins, Alcoa, TN (US)

(73) Assignees: Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/589,341

(22) Filed: Jan. 31, 2022

(51) Int. Cl.
*A01H 5/08* (2018.01)
*A01H 6/74* (2018.01)

(52) U.S. Cl.
USPC ..... Plt./174
CPC ..... *A01H 6/7418* (2018.05)

(58) Field of Classification Search
USPC ..... Plt./174
CPC ..... A01H 5/0875
See application file for complete search history.

(56) References Cited

U.S. PATENT DOCUMENTS

| | | | |
|---|---|---|---|
| PP7,197 | P | 3/1990 | Luby et al. |
| PP22,228 | P3 | 11/2011 | Brown et al. |
| PP23,337 | P3 | 1/2013 | Cummins et al. |
| PP24,073 | P3 | 12/2013 | Cummins et al. |

OTHER PUBLICATIONS

Mazzola, (1998). "Elucidation of the microbial complex having a causal role in the development of apple replant disease in Washington," Phytopathology, 88(9):930-938.
Unpublished U.S. Appl. No. 17/589,324, filed Jan. 31, 2022 titled "Apple Tree Rootstock Named 'G.484',".
Unpublished U.S. Appl. No. 17/589,353, filed Jan. 31, 2022 titled "Apple Tree Rootstock Named 'G.257',".

*Primary Examiner* — Kent L Bell
(74) *Attorney, Agent, or Firm* — Morrison & Foerster LLP

(57) ABSTRACT

A new and distinct variety of apple tree rootstock *Malus domestica* x *Malus robusta* hybrid 'G.66' is described herein. The new variety is a productive, yield efficient, semi-dwarfing rootstock that is resistant to fire blight (*Erwinia amylovora*) and crown rot (*Phytophthora cactorum*). The 'G.66' rootstock is useful in that it can be propagated clonally and used as a rootstock or root system for apple trees as well as for interstems of apple trees.

9 Drawing Sheets

STATEMENT REGARDING FEDERAL FUNDING

This invention was made with United States government support under a United States Department of Agriculture—Agricultural Research Station Cooperative Research and Development Agreement, Sponsor's Contract Number 58-3K95-M-1031. The government has certain rights in the invention.

Genus and species: *Malus domestica* x *Malus robusta* hybrid.

Variety denomination: 'G.66'.

BACKGROUND OF THE INVENTION

I. Field and Utility Summary

The invention described here is a new variety of apple tree rootstock, *Malus domestica* x *Malus robusta* hybrid, hereinafter referred to as 'G.66'. This new apple tree is useful as it can be propagated clonally and used as a root system or interstem for apple trees. This new variety is a dwarfing rootstock that is resistant to fire blight and crown rot. It promotes early bearing to grafted scions, it features strong graft unions with most scions, and it is productive as a rootstock or interstem of apple trees.

II. Cultivation Summary

'G.66' originated from a planned cross (*Malus domestica* x *Malus robusta* hybrid) in 1976 in Geneva, N.Y.

SUMMARY OF THE INVENTION

The present invention relates to a new and distinct variety of apple tree rootstock named 'G.66'. The 'G.66' apple tree rootstock is a semi dwarfing rootstock that is resistant to fire blight (*Erwinia amylovora*) and crown rot (*Phytophthora cactorum*). The 'G.66' rootstock is useful in that it can be propagated clonally and used as a rootstock or root system for apple trees as well as for interstems of apple trees. Whereas 'G.66' rootstock is a hybrid from a cross between 'PK 14' (Not patented) and 'Robusta 5' (Not patented), it is distinct from its parent cultivars in terms of dwarfing. The apple tree rootstock 'G.66' is less dwarfing than 'PK 14' and more dwarfing than the non-dwarfing parent 'Robusta 5'. Unlike 'PK 14', 'G.66' is resistant to fire blight. Although 'G.66' is in the same dwarfing rootstock class as 'Mailing 7' (Not patented), it is distinguishable from 'Mailing 7' because 'G.66' is resistant to fire blight and precocious whereas 'Mailing 7' is susceptible and non-precocious.

I. BREEDING HISTORY

In the spring of 1976, pollen from a *Malus robusta* 'Robusta 5' apple tree was applied to emasculated flowers of a *Malus domestica* 'PK 14' apple tree at a research farm (Geneva, N.Y.). In the fall of 1976, approximately 500 seeds resulting from this pollination were extracted from mature fruit derived from this cross. In the winter of 1976-1977, the seeds were stratified and planted in large flats under conditions effective to germinate seeds and obtain seedlings. When germinated seedlings were about 2.5 cm tall they were inoculated with a mixture of isolates of the oomycete *Phytophthora cactorum* (the causal agent of crown and root rots). The flats were flooded to mid-hypocotyl level and kept at 23° C. for one week. Surviving seedlings were transplanted into individual pots.

In the summer of 1977, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #006 was one of the survivors of this battery of inoculations from the same cross and eventually was named 'G.66'. All the surviving plants were transplanted to a research field (Geneva, N.Y.) in the fall of 1977 and allowed to grow side shoots for propagation/evaluation. In 1980, 'G.66' was evaluated for rooting ability, lack of spine production, and low root brittleness in a layering bed (stool bed). In 1983, 4 finished trees with 'G.66' rootstock were planted in a first test orchard on an apple research farm (Geneva, N.Y.) with *Malus domestica* cv. 'Northern Spy' (Not patented) grafted onto this rootstock as the scion cultivar. This rootstock performed well (top 20% of many rootstocks tested) in these first test trials and during 1990-1993 more material was propagated by stool bed and nursery to be entered into new trials in a research farm (Geneva, N.Y.) with *Malus domestica* cv. 'Empire' (Not patented) as the scion cultivar. The 'G.66' rootstock performed well with all the scion cultivars that were tested. In August of 2002, several rootstock liners of 'G.66' were budded with 15 different scion cultivars to test graft union compatibility—the test results showed that 'G.66' was compatible with all the cultivars tested. In summer 2002, 40 rootstock liners were inoculated with four different strains of fire blight (ten liners per strain) in a research greenhouse (Geneva, N.Y.) of the U.S. Department of Agriculture Agricultural Research Service. As a result, the apple rootstock 'G.66' was classified as immune to two of the strains tested and moderately resistant to the other two strains of fire blight.

II. ASEXUAL REPRODUCTION

Asexual reproduction of the 'G.66' apple rootstock has been achieved using the traditional method of clonally propagating apple rootstocks. In particular, the original seedling of the 'G.66' apple rootstock was planted in a research nursery (Geneva, N.Y.) and allowed to develop into a "mother plant." The 'G.66' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.66' apple rootstock variety has been asexually reproduced by root cuttings, by budding and grafting onto seedling and clonal rootstocks, and by tissue culture.

III. STABILITY

Observations of trees from these propagations indicate that all trees have proven true to type and identical in all appearances to the original tree through successive generations of asexual reproduction.

IV. COMPARISONS WITH PARENTAL AND REFERENCE VARIETIES

The seed parent *Malus domestica* 'PK 14' is a dwarfing rootstock, i.e., trees grown on this rootstock are 30 to 35 percent the size of a standard self-rooted seedling tree. 'PK 14' is known to induce good precocity to the scion (i.e., the ability to induce early reproductive development in the scion) and has high yield efficiency. 'PK 14' plants produce no spines, are fairly well anchored, are a very cold hardy rootstock and have resistance to crown and root rot caused by *Phytophthora cactorum*. However, 'PK 14' is susceptible to the woolly apple aphid (*Eriosoma lanigerum*) and to fire blight (*Erwinia amylovora*). 'PK 14' produces high anthocyanin levels in leaf venations, phloem and fruit skin.

The pollen parent *Malus robusta* 'Robusta 5' is a non-dwarfing rootstock, i.e. trees on this rootstock are the same size as a standard self-rooted tree. 'Robusta 5' does not induce precocity to the scion and is not highly yield efficient. Juvenile plants of 'Robusta 5' produce many spines. 'Robusta 5' breaks buds very early in the spring and is winter hardy. It has displayed resistance to powdery mildew (*Podosphaera leucotricha*), fire blight, and is immune to the woolly apple aphid. Further, 'Robusta 5' has shown tolerance to the specific replant disease complex.

The 'G.66' apple rootstock of the present invention has a combination of qualities that distinguishes it from its parental plants (i.e., 'PK 14' and 'Robusta 5'). For example, although 'G.66' has dwarfing properties derived from 'PK 14', it is different from its dwarfing parent (i.e., 'PK 14') because it produces a tree that is 45 to 55 percent of the size of a standard self-rooted seedling tree. Thus 'G.66' belongs to a different dwarfing vigor class than its 'PK 14' parent. 'G.66' shares similarities with 'PK 14' in that they both induce precocity to the scion, are highly yield efficient and winter hardy. Similarly to 'PK-14' apple rootstock 'G.66' produces high anthocyanin (red) levels in leaves, stems (phloem) and fruit.

With regard to its 'Robusta 5' parent, 'G.66' is distinguishable in that it is a dwarfing rootstock and is highly yield efficient, whereas 'Robusta 5' is not. However, like 'Robusta 5', 'G.66' is resistant to fire blight and tolerant to powdery mildew. In addition, 'G.66' has been shown to have some tolerance to the replant disease complex. Unlike its 'Robusta 5' parent, 'G.66' is susceptible to the woolly apple aphid (*Eriosoma lanigerum*).

'G.66' has dwarfing (vigor control) characteristics that are similar to the industry standard of *Malus domestica* 'Mailing 7' (Not patented) and is generally placed in the same category as 'Mailing 7' in terms of dwarfing class. However, 'G.66' is more precocious and yield efficient than 'Mailing 7'. 'G.66' is resistant to fire blight whereas 'Mailing 7' is not.

DESCRIPTION OF THE FIGURES

New apple tree rootstock 'G.66' is illustrated by the accompanying photographs. The ages of the trees depicted in the photographs are noted below. The colors shown are as true as can be reasonably obtained by conventional photographic procedures.

DETAILED BOTANICAL DESCRIPTION OF THE INVENTION

Figure 1:
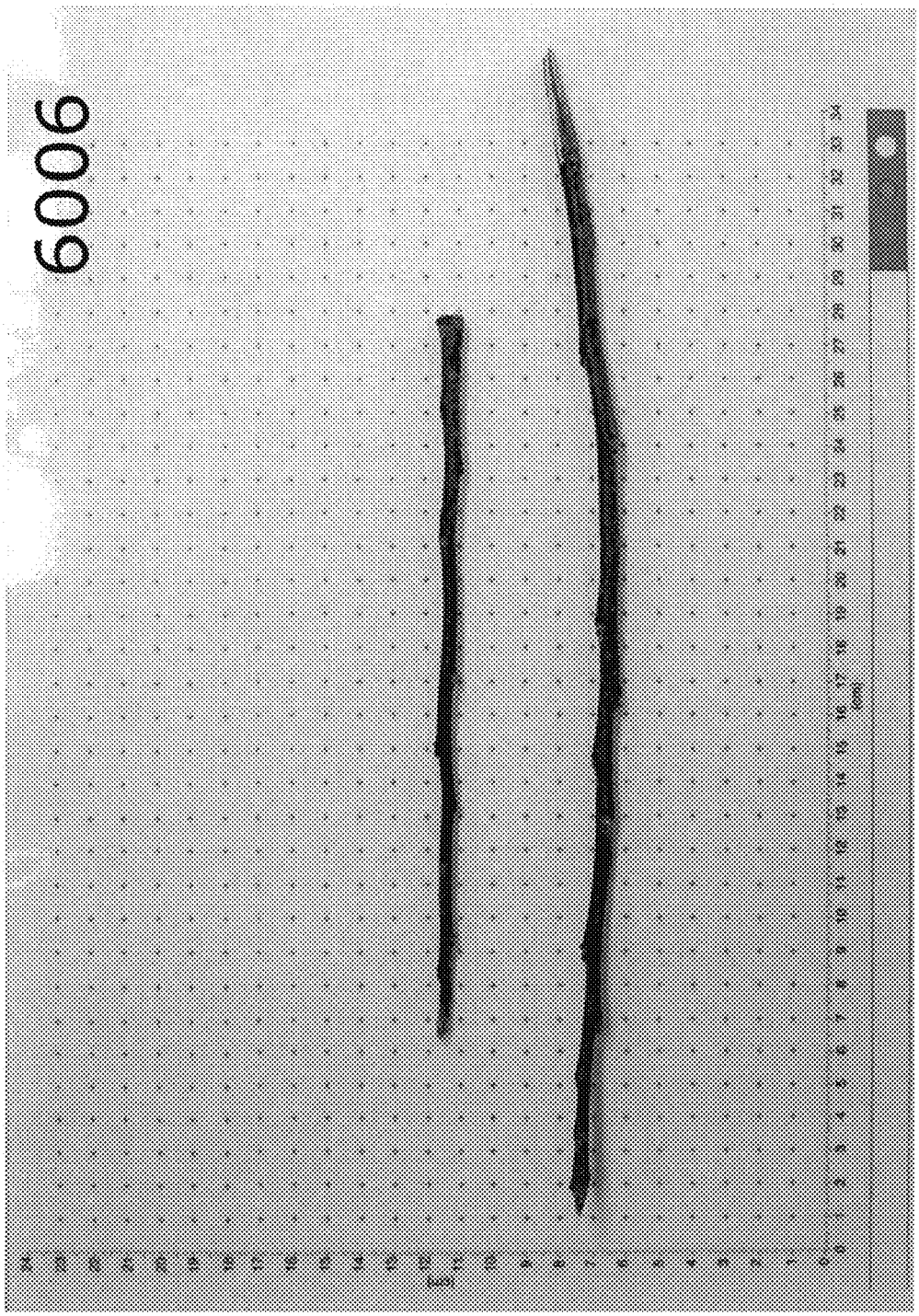
FIG. 1 shows dormant shoots (including buds and bark).
Figure 2:
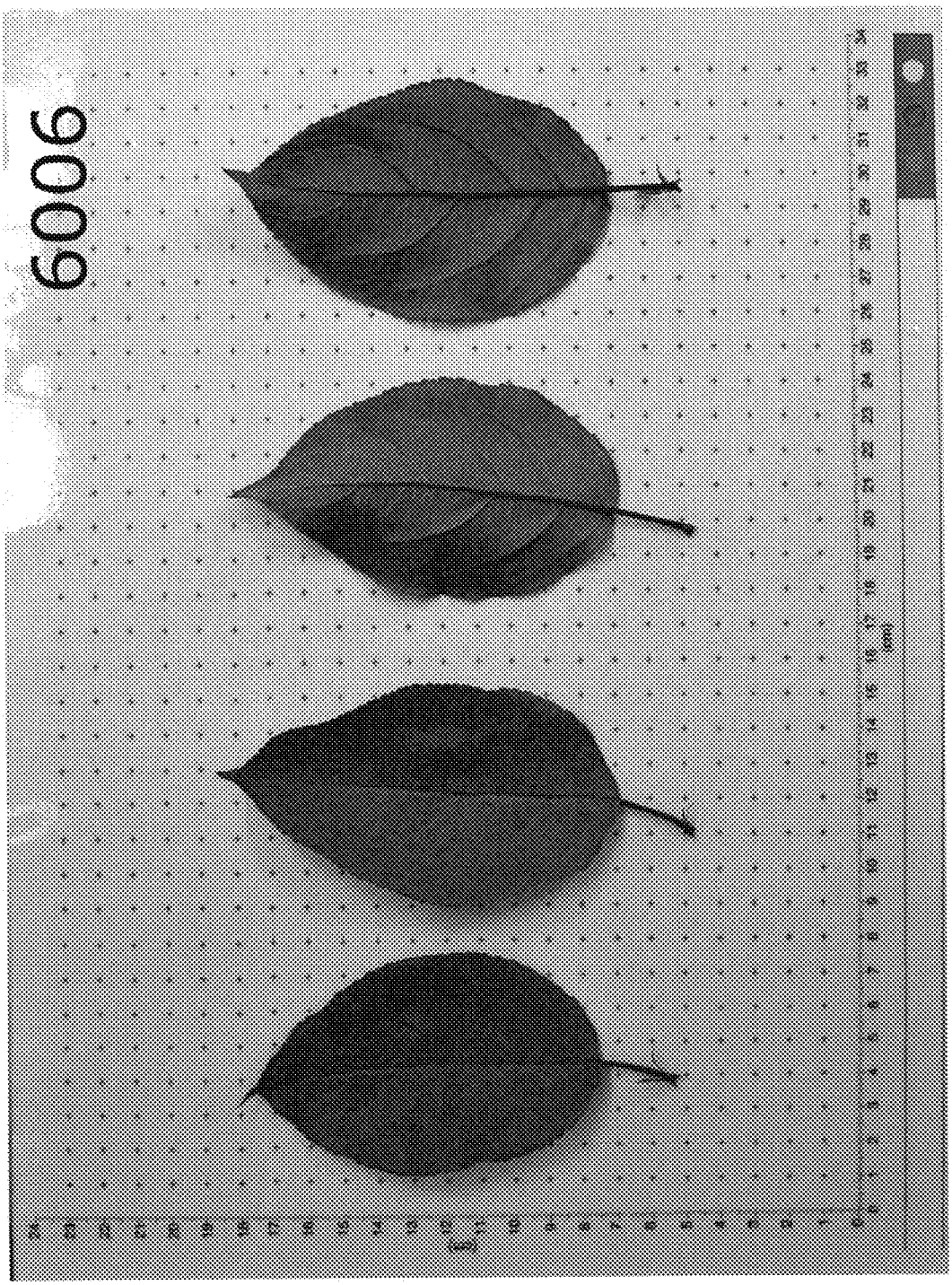
FIG. 2 shows abaxial (lower) and adaxial (upper) laminae of leaves.
Figure 3:
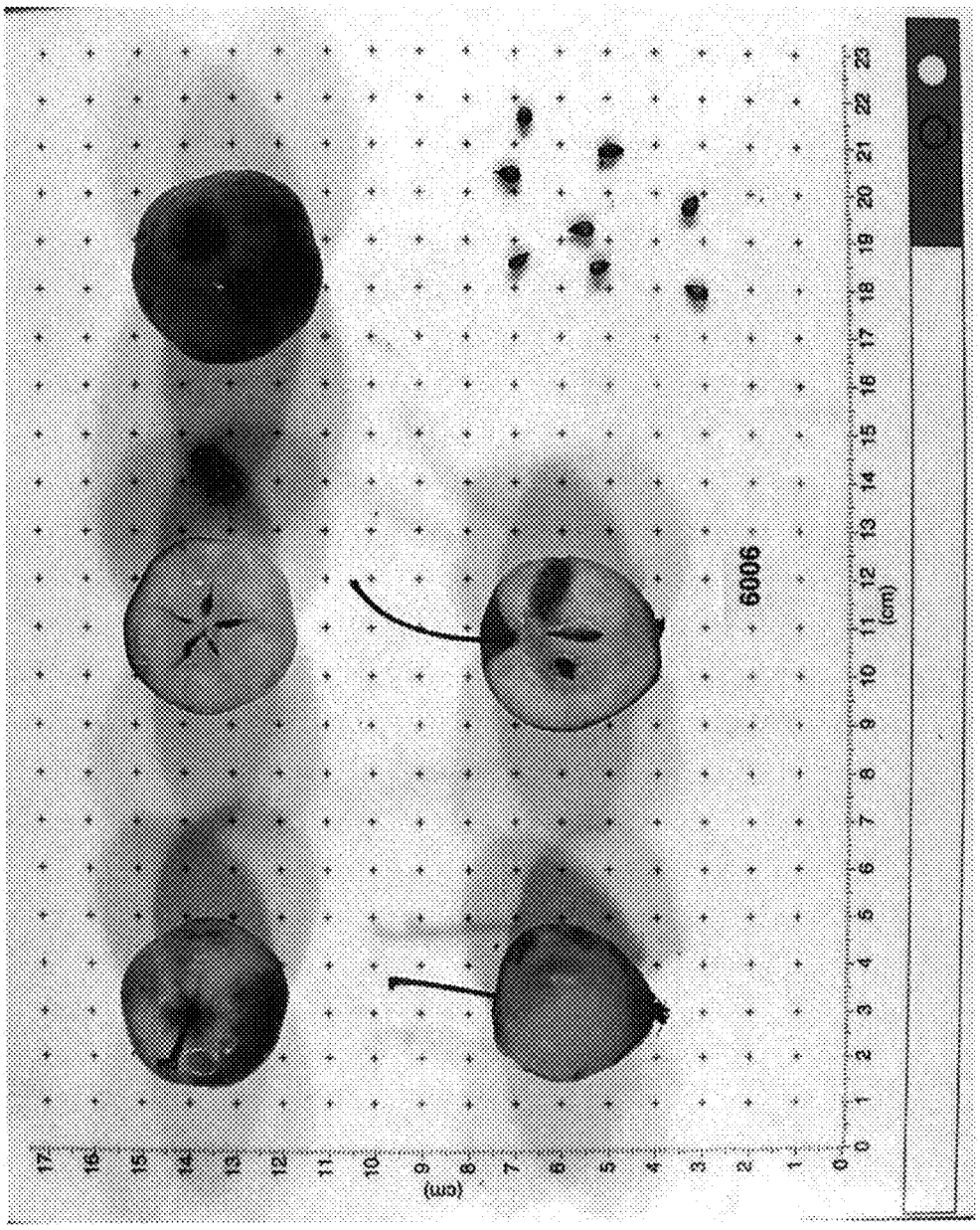
FIG. 3 shows interior and exterior of fruit and seeds.
Figure 4:
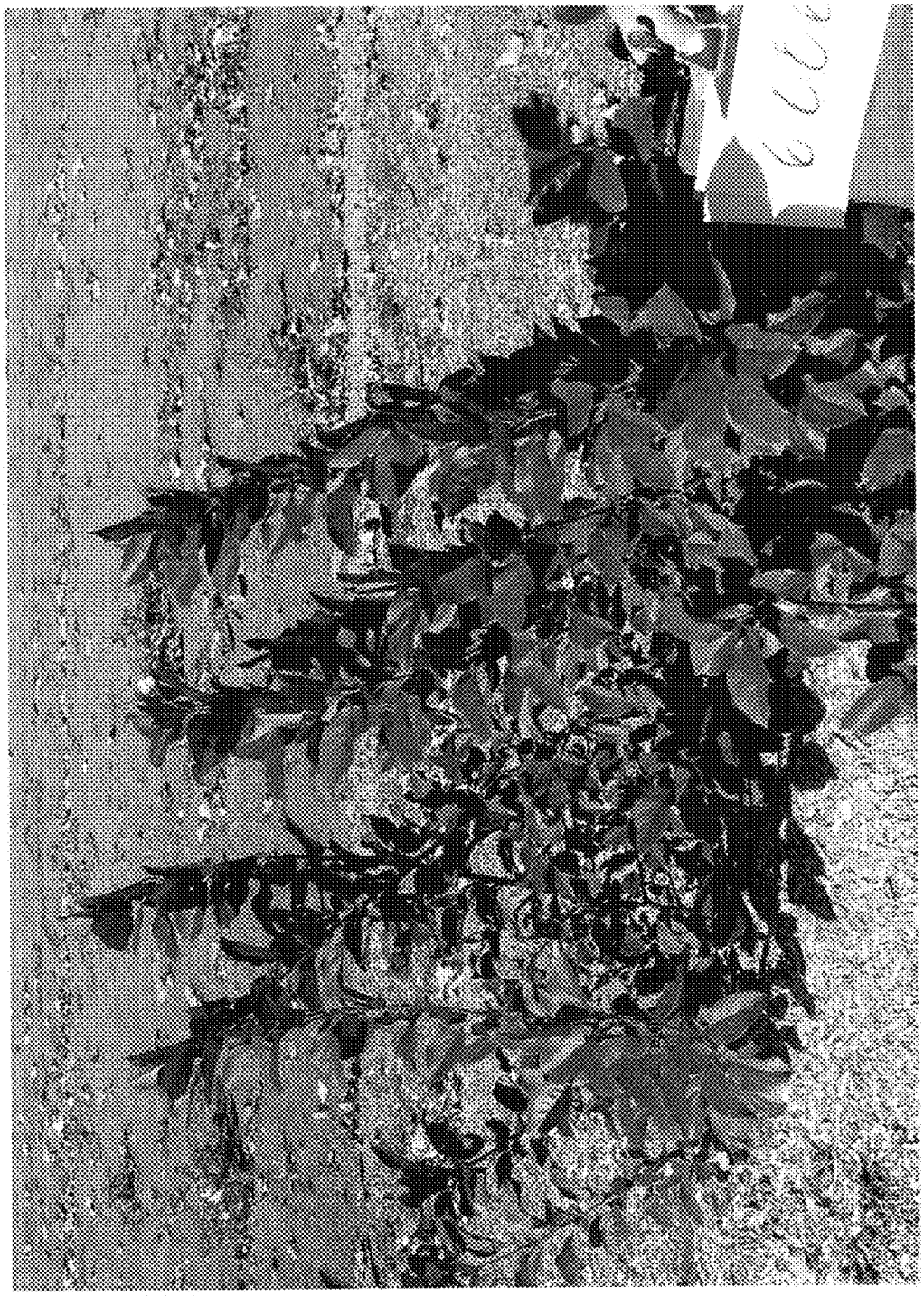
FIG. 4 shows a stool propagation bed with fully developed shoots.
Figure 5:
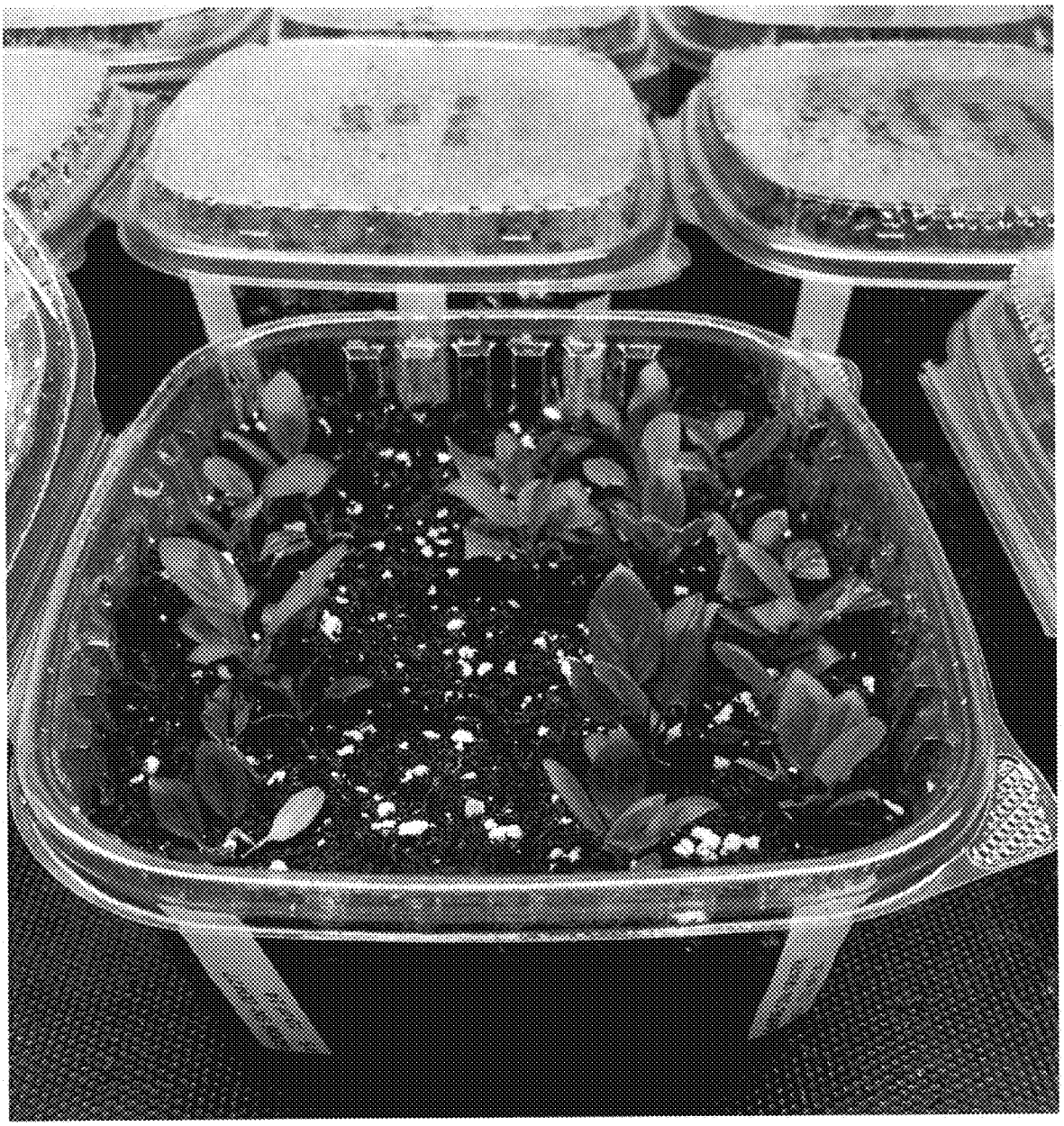
FIG. 5 shows micro-shoots obtained by in-vitro propagation.
Figure 6:
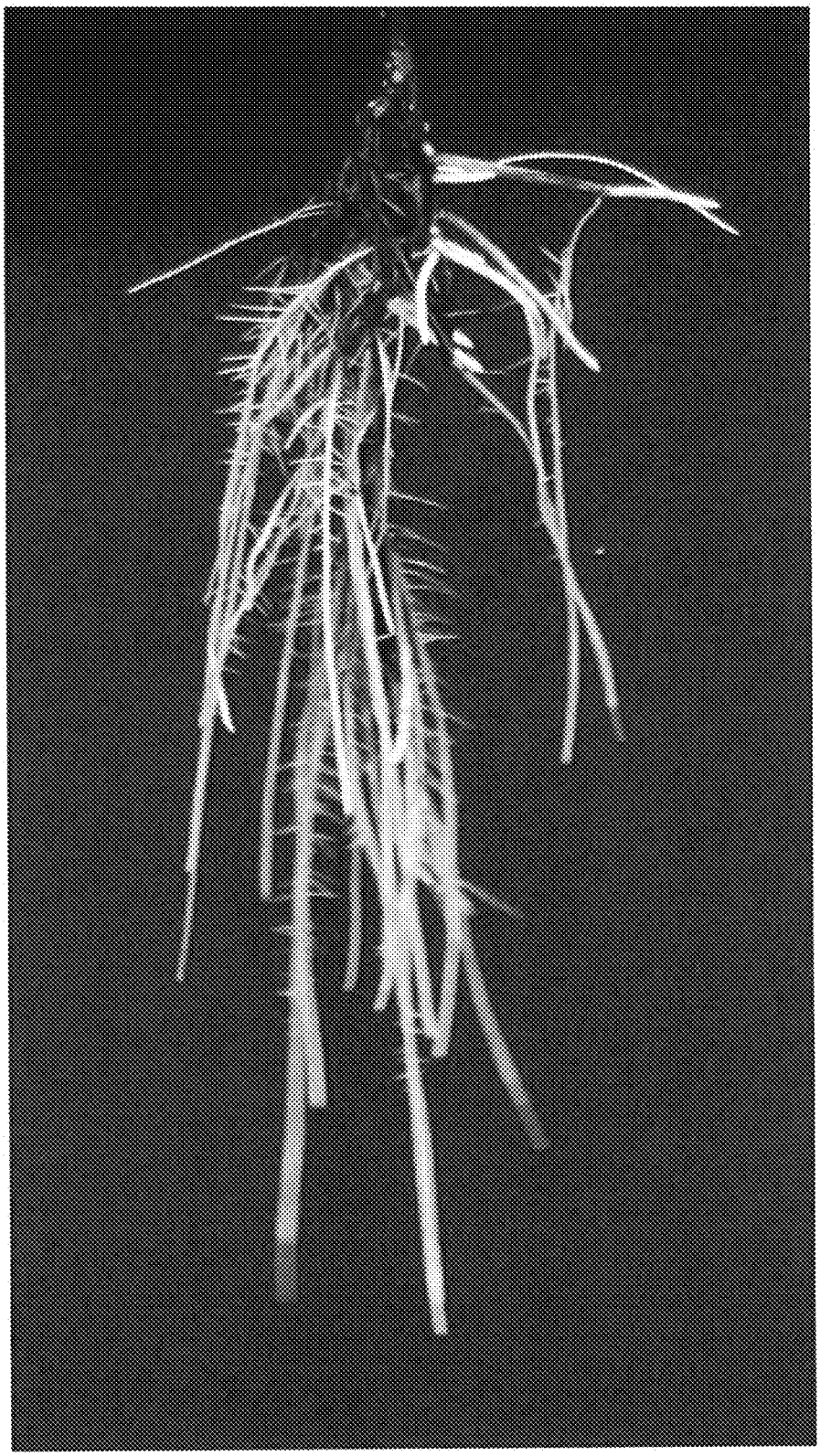
FIG. 6 shows roots grown in aeroponics.
Figure 7:
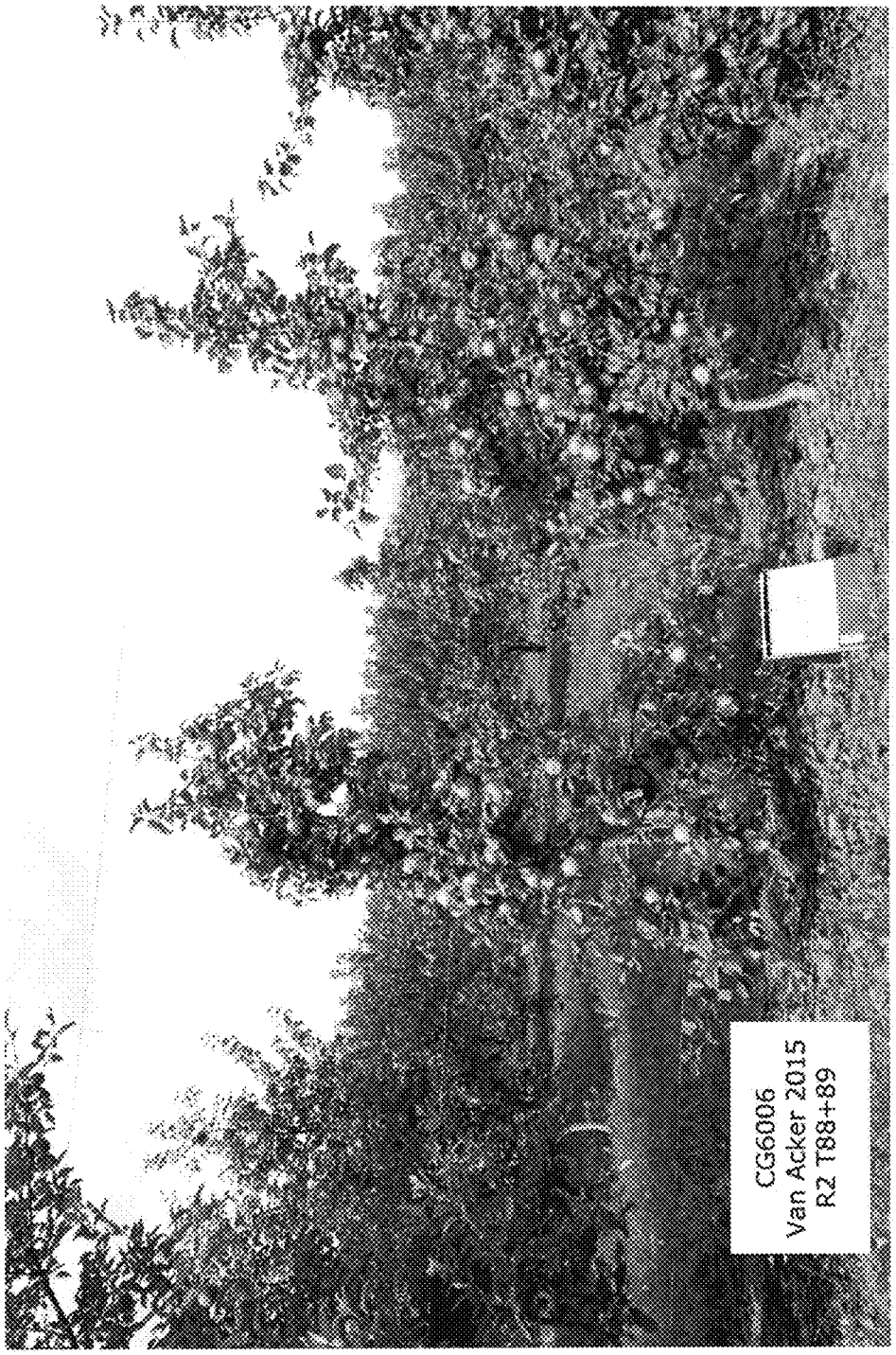
FIG. 7 shows 5 year old trees grafted on 'G.66'.
Figure 8:
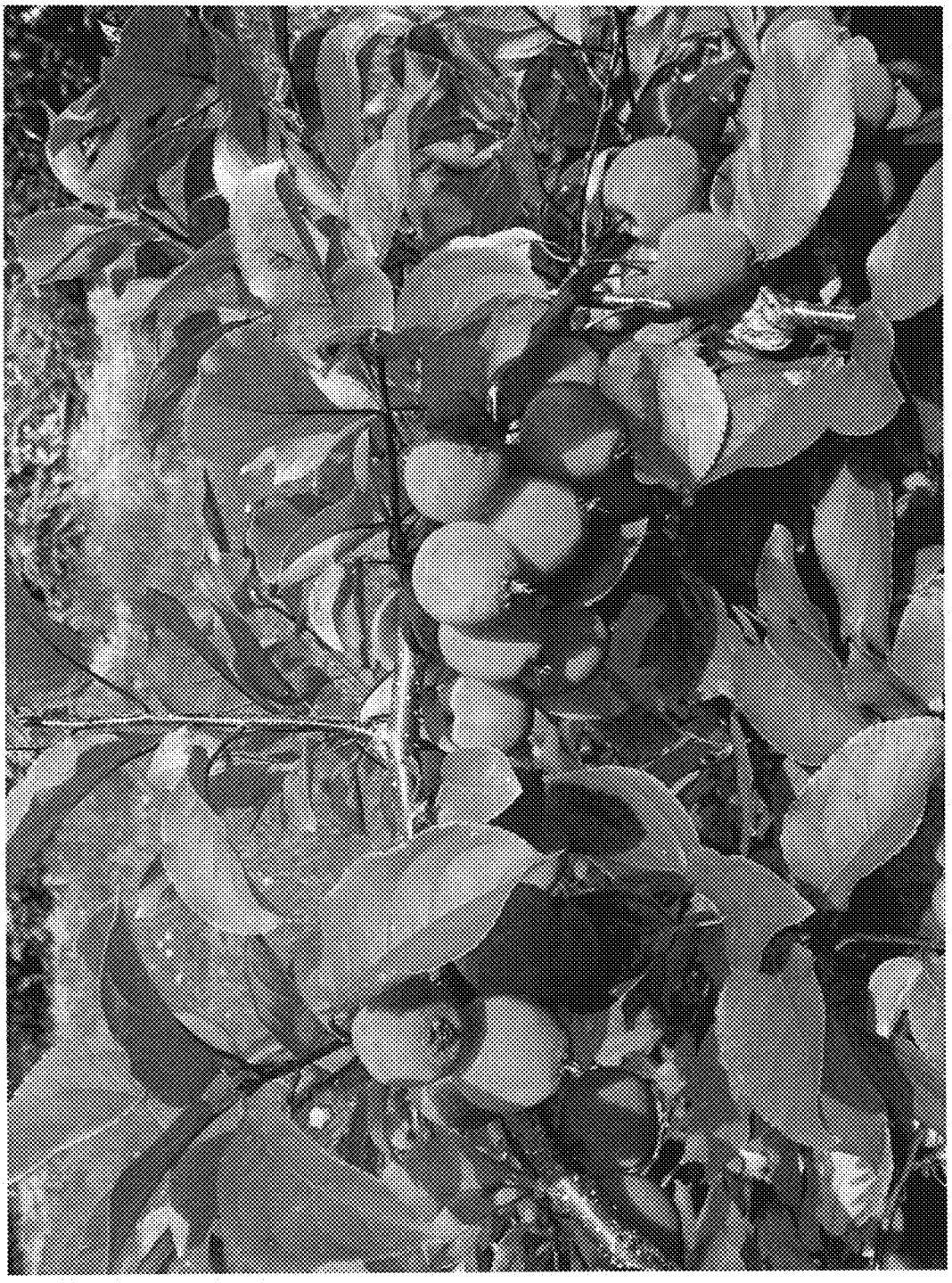
FIG. 8 shows maturing fruit and leaves.
Figure 9:
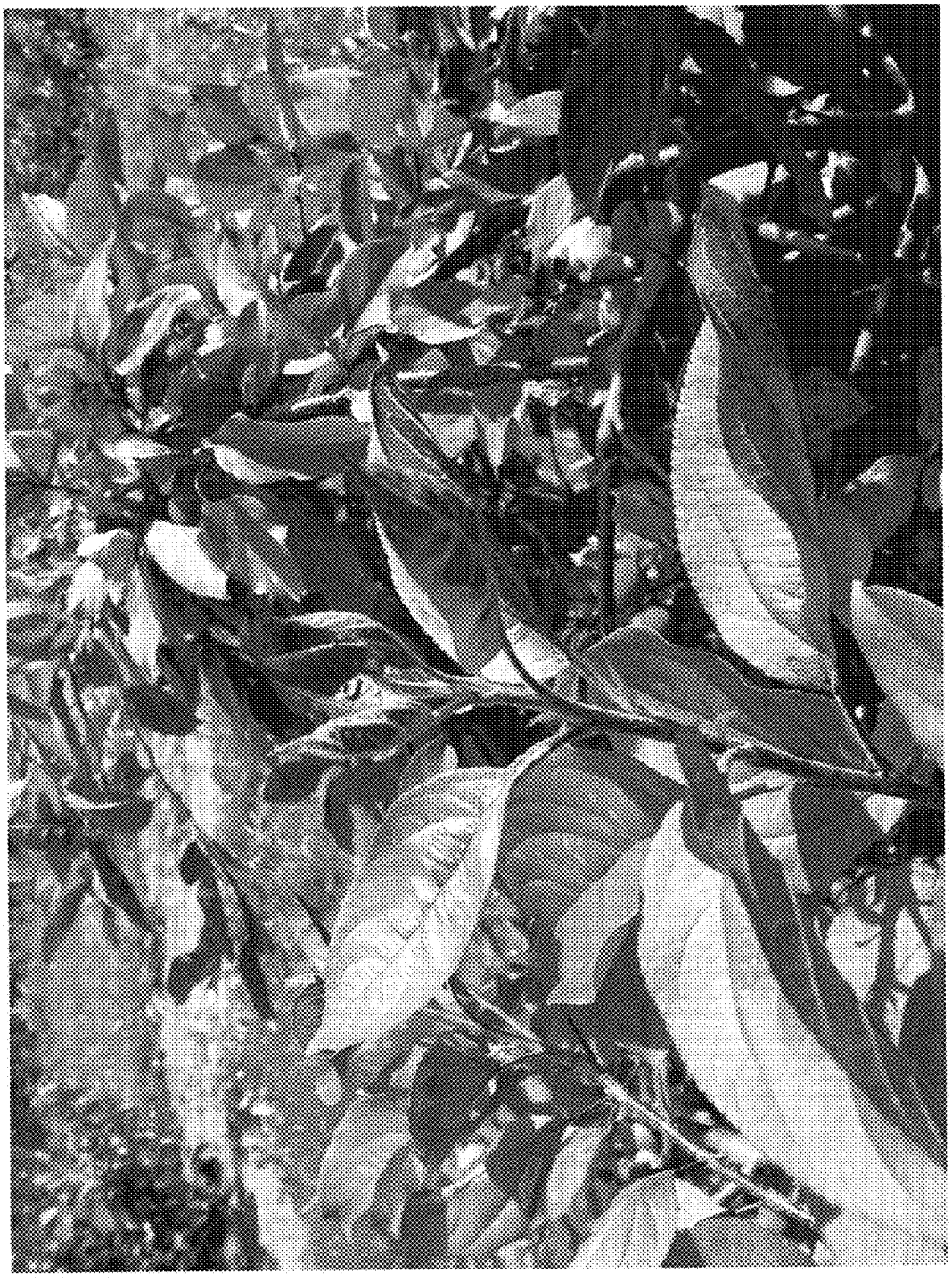
FIG. 9 shows high anthocyanin levels in developing leaves.

The following description of apple tree rootstock 'G.66' contains references to color names taken from The Royal Horticultural Society Colour Chart (R.H.S.), 2001 edition. Botanical descriptions follow the Manual of Cultivated Plants (Bailey, 1949).

Tree:

*Habit*.—A self-rooted tree of 'G.66' is a shrub typically standing about 1.5-2 meters tall by about 2 meters wide when 7 years old. Multiple trunks-shoots can develop from suckers (adventitious shoots arising from surface roots). Canopy can be somewhat spreading. Rootstock liners planted in the nursery stop apical growth mid-season. The apical bud in these plants is pubescent Greyed-Purple (RHS 187A to 187B).

*Productivity*.—In an intermediate trial performed at a research farm (Geneva, N.Y.), the 'G.66' rootstock received the cultivar 'Golden Delicious' (Not patented) (*Malus domestica*) as the scion and was compared to the *Malus domestica* check rootstocks 'Mailing 9' ('M.9 EMLA'; Not patented), 'Mailing 26' ('M.26'; Not patented) and 'Mailing 7' ('M.7'; Not patented). 'G.66' was shown to have statistically similar ($p \leq 0.05$) yield efficiency (kg yield/$cm^2$ trunk cross sectional area) than 'Mailing 9' and 'Mailing 26' rootstocks while featuring the largest cumulative yield.

*Precocity*.—Scion cultivars budded on 'G.66' exhibit similar precocity (early bearing induction) as those budded on 'Mailing 26'.

*Fertility* (*fecundity*).—The 'G.66' plant produces flowers and fruits regularly.

Dormant shoots (buds and bark):

*Dormant mature shoots*.—Color: Greyed-Purple (RHS N186A to N186B). Texture: Some pubescence which gradually disappears in older tissues. Size: 30-60 cm long; may have some spines. Diameter: Typical, mature one year dormant shoots have a diameter ranging from 12-22 mm.

*Axillary buds*.—Size: 4-5 mm long and 3 mm wide with pubescence on the apices. Shape: Obtuse, sessile, somewhat protruding and flattened. Texture: Some pubescence.

*Bark on three-year-old shoots*.—Color: Greyed-Purple (RHS 197A). Lenticels: Color: Greyed-Orange (RHS 171B to 171C). Size: 0.3-0.4 mm in diameter. Quantity: 1-2 lenticels per $cm^2$.

Leaves:

*Mature leaves*.—Leaf arrangement: Alternate. Shape: Simple, recurved, oblong-ovate. Size: Length: 110 mm. Width: 60 mm at the widest point. Laminae: Somewhat wavy. Apex: Acuminate. Base: Nearly symmetrical rounded. Margin: Serrated, with about 4 serrations per cm. Upper surface: Color: Green (RHS 141B) with Greyed-Purple (RHS 185B) venations. Texture: Glabrous and translucent. Lower surface: Color: Yellow-Green (RHS 146B) with Greyed-Purple (RHS184C to 184D) hues and venations. Texture: Somewhat pubescent. Venation: Netted. Venation color: Greyed-Purple (RHS184C to 184D) in the larger venations transitioning to Greyed-Red (182D) in smaller veins. Leaf poise: 25°-45° from the shoot, depending on shoot orientation. Stipules: Length: 8 mm. Width: 2 mm. Color: Green (RHS 141B) to Greyed-Purple (RHS184C to 184D). Petioles: Diameter: 3 mm. Length: 18-25 mm. Texture: Glabrous (smooth). Color: Greyed-Purple (RHS 184A to 184C) depending on low or high exposure to light.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot. Pubescence color: Greyed-Green (RHS 196C). Color of scales beneath pubescence: Greyed-Purple (RHS N186A). Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals*.—Size: Length: 25 mm. Width: 18 mm. Shape: Spatulate. Apex: Obtuse. Margin: Smooth. Texture: Smooth. Arrangement: Intermediate. Color: Closed petals: Red (RHS 54A) (Abaxial surface). Opening petals: Flowers undergo a transition as they are opening and colors become less intense. Open petals: Red-Purple (RHS 64D) with Red (RHS 54A) striations in some of the petals (Adaxial surface).

*Reproductive organs*.—Pistils: Length: 6 mm. Color: Red (RHS 52B). Stamens: Length: 4 mm. Color: Red (RHS 52A). Anther color: Greyed-Yellow (RHS 162A).

Fruit:

*Mature fruit*.—Size: Height: 35-40 mm. Diameter: 30-35 mm. Shape: Obloid. Color: Orange-Red skin (RHS 30B) with Red (RHS 43B) blush overtones depending on the exposure to the sun. Sepals: Persisting on a protruding calyx. Flesh: Taste: Astringent (not meant for consumption). Color: Orange-Red (RHS 30A to 30D) bleeding from skin and core. Pedicels: Length: 20-27 mm. Diameter: 0.8-1.2 mm. Texture: Glabrous (smooth). Color: Greyed-Purple (RHS 184A to 184C). Seed: Color: Greyed-Red (RHS 179A), translucent. Shape: Tear drop shape. Texture: Glabrous (smooth). Size: Length: 3 mm. Diameter: 4.5 mm at the widest point. Number: Generally five seed per fruit.

Disease resistance: As described above, the 'G.66' rootstock of the present invention exhibits resistance to fire blight. The percent lesion measured after inoculation of potted liners in the greenhouse using four different strains of *E. amylovora* was negligible for two of the strains and moderate for the other two, indicating a specific resistance to the bacterium. The 'G.66' rootstock, having survived the inoculation with crown and root rot, is also considered resistant to crown and root rots caused by *Phytophthora cactorum.*

What is claimed is:

1. A new and distinct variety of apple tree named 'G.66' as herein described and illustrated.

* * * * *